United States Patent
Zhang (10) Patent No.: US 9,012,185 B2
(45) Date of Patent: Apr. 21, 2015

(54) THERMAL CYCLING DEVICE WITH PHASE CHANGING FLUIDS

(71) Applicant: Pyro-E, LLC, San Jose, CA (US)

(72) Inventor: Rui Zhang, Oaks, PA (US)

(73) Assignee: Pyro-E, LLC, San Jose, CA (US)

( * ) Notice: Subject to any disclaimer, the term of this patent is extended or adjusted under 35 U.S.C. 154(b) by 0 days.

(21) Appl. No.: 13/687,768

(22) Filed: Nov. 28, 2012

(65) Prior Publication Data

US 2013/0137105 A1     May 30, 2013

Related U.S. Application Data (60) Provisional application No. 61/563,858, filed on Nov. 28, 2011.

(51) Int. Cl.
*C12P 19/34*     (2006.01)
*G01N 21/75*     (2006.01)
*C12Q 1/68*     (2006.01)
*B01L 7/00*     (2006.01)

(52) U.S. Cl.
CPC . *C12P 19/34* (2013.01); *B01L 7/52* (2013.01); *G01N 21/75* (2013.01); *C12Q 1/68* (2013.01); *B01L 2300/0829* (2013.01); *B01L 2300/1855* (2013.01)

(58) Field of Classification Search
CPC ................................ C12P 19/34; G01N 21/75
USPC ............. 435/91.2, 6.12, 174, 283.1; 422/417, 422/50, 430, 68.1, 500, 129, 138, 600
See application file for complete search history.

(56) References Cited

U.S. PATENT DOCUMENTS

| | | | |
|---|---|---|---|
| 4,587,851 A * | 5/1986 | Mortberg | 73/724 |
| 6,278,111 B1 * | 8/2001 | Sheehan et al. | 250/288 |
| 6,468,782 B1 * | 10/2002 | Tunnacliffe et al. | 435/260 |
| 6,472,186 B1 | 10/2002 | Quintanar | |
| 6,640,891 B1 * | 11/2003 | Oldenburg | 165/253 |
| 8,003,370 B2 | 8/2011 | Maltezos | |
| 8,105,783 B2 | 1/2012 | Handique | |
| 2007/0026444 A1 | 2/2007 | Heff | |
| 2009/0275113 A1 | 11/2009 | Maltezos et al. | |
| 2010/0107436 A1 * | 5/2010 | Velardi et al. | 34/284 |
| 2010/0261230 A1 | 10/2010 | Liu et al. | |

* cited by examiner

*Primary Examiner* — Ardin Marschel
(74) *Attorney, Agent, or Firm* — Casimir Jones SC (57) ABSTRACT

The invention provides systems, devices, and methods for heating and cooling chemical or biological samples, such as genetic materials during Polymerase Chain Reaction ("PCR"). The systems, devices, and methods comprise use of a fluid that performs repeated heating and cooling cycles, e.g., 'thermal cycling', on sample reactants with a phase changing fluid during evaporation and condensation. The systems, devices, and methods eliminate the need for a heating block as a means to obtain fast and uniform thermal cycling. The disclosure also describes the use of an optical system in conjunction with the thermodynamic cycler for real-time detection. Ultimately, uniformity and speed of the thermodynamic cycler provides for higher sensitivity and throughput of gene replication and detection.

7 Claims, 7 Drawing Sheets

THERMAL CYCLING DEVICE WITH PHASE CHANGING FLUIDS

This application claims the priority benefit of provisional patent application Ser. No. 61/563,858, filed Nov. 28, 2011, the disclosure of which is herein incorporated by reference in its entirety.

FIELD

The invention provides systems, devices, and methods for heating and cooling chemical or biological samples, such as genetic materials during Polymerase Chain Reaction ("PCR"). For example, methods comprise use of a fluid that performs repeated heating and cooling cycles, i.e., 'thermal cycling', on sample reactants with a phase changing fluid during evaporation and condensation. The method can eliminate the use of a heating block as a means to obtain fast and uniform thermal cycling.

BACKGROUND

Invented in 1983 by Kary Mullis, the advent of Polymerase Chain Reaction (PCR) is recognized as one of the most important scientific developments of the twentieth century. PCR has revolutionized molecular biology through vastly extending the capability to identify and reproduce genetic materials such as DNA. Nowadays PCR is routinely practiced in medical and biological research laboratories for a variety of tasks, such as the detection of hereditary diseases, the identification of genetic fingerprints, the diagnosis of infectious diseases, the cloning of genes, paternity testing, and DNA computing. The method has been automated through the use of thermal stable DNA polymerases and a machine commonly referred to as "thermal cycler."

The conventional thermal cycler has several intrinsic limitations. Typically a conventional thermal cycler contains a metal heating block to carry out the thermal cycling of reaction samples. Because the metal block has a large thermal mass and the sample vessels have low heat conductivity, cycling the required levels of temperature is inefficient. The ramp time of the conventional thermal cycler is generally not rapid enough and inevitably results in undesired non-specific amplification of the target sequences. Temperature overshoot or undershoot pass temperature set points during ramping also reduced the desired outcome during sample analysis. The suboptimal performance of a conventional thermal cycler is also due to the lack of thermal uniformity during cycling large sample sets, as widely acknowledged in the art. Furthermore, the conventional real-time thermal cycler system carries optical detection components that are bulky and expensive.

As an alternative to the heating block design, other methods also have shortcomings in speed and uniformity. For example, force air or liquid cyclers lack the temperature uniformity between sample wells due to the fact that fluid velocity and temperature is reduced across the multitude of DNA sample typically used in PCRs (Maltezos et al., U.S. Pat. No. 8,003,370). Also, PCR microfluidic chips can achieve up to 15° C./sec ramping rates due to the small sample volumes (Handique, U.S. Pat. No. 8,105,783). However, these lab-on-chip devices currently remain as custom solutions due to bio-incompatibility and surface chemistry issues that interfere with the polymerase activity. Moreover, constant temperature methods exist, e.g., LAMP and TMA, to eliminate the need for a thermal cycler. These isothermal methods, however, requires different polymerase and preparation protocols that are less familiar to many geneticists or molecular biologists.

Quintanar (U.S. Pat. No. 6,472,186) discloses a thermal cycler using pressurized gas flow. The patent describes a method in which a single-phase fluid performs the thermal cycles during the PCR process. The patent outlined the used of first and second heat transfer gases, under pressure, as a means of providing fast and uniform heat transfer to a plurality of samples. These forced convection methods using air only marginally improve performance of a PCR platform given that the heat transfer rates for gas is much lower than liquids or phase-changing fluids.

Heff (US Pat. Publ. No. 20070026444) discloses a thermal cycler by thermodynamic method. The application describes a method in which adiabatic work is performed on analyte samples inside the reaction vessel. One embodiment uses a piston to drive pressure and temperature cycles. Although technically sound, the weakness of the design is related to the difficulty of manufacturing sealed pistons that can operate in a reliable manner for the large pressures required. Also cross-contamination is likely to occur during handling and operating the movable piston inside the sample vessels. This drawback reduces the usability of an unfamiliar design and severely limits the commercialization appeal of the technology.

There thus remains a considerable need for an alternative thermal cycler technology. A desirable device would allow (a) rapid, precise and uniform transfer of heat to effect a more specific amplification reaction of nucleic acids; and/or (b) monitoring of the progress of the amplification reaction in real time; and/or (c) contaminant-free and user-friendly operation. The present invention satisfies these needs and provides related advantages as well. The present thermal cycler provides unprecedented cycling rates while retaining the usability of conventional PCR and real-time PCR platforms.

SUMMARY

In some embodiments, the present invention provides a thermal cycler apparatus that provides rapid heating and cooling methods for use with analyte samples in the PCR procedure. Methods according to one or more aspects can provide significantly faster temperature ramping rates and uniformity than other PCR systems presently in-use. The thermodynamic cycling method alters the pressure of a working refrigerant fluid such as water, R135, or any other type of refrigerant fluid. In some embodiments, no adiabatic work is done directly on the analyte solution inside its containing vessel. In some embodiments, the analyte solution is contained within plastic or metallic vessel.

In some embodiments, the systems, devices, and methods employ the use of valves to actuate the pressure of the working fluid during thermal cycling. During valve opening, the working refrigerant undergoes phase change. Substantial improvement over existing technology is attributed to the high heat transfer rate of evaporation and condensation of the refrigerant to conduct heating and cooling. By directly heating and cooling of DNA sample vessels, the performance gain is contemplated to be substantial over other PCR platforms. Also, the concept differs from other air or liquid cyclers in that the temperature ramping is caused by pressure change, not fluid flow. This allows superb thermal cycling speeds and temperature uniformity.

In some embodiments, the thermal cycler device comprises three insulated pressure chambers to withstand substantially large pressures. A phase changing fluid such as either water or another type of refrigerant is shuttled between the three insulated chambers. One chamber holds low-pressure vapor or vapor-liquid mixture at low temperature. Another chamber holds high-pressure vapor, or vapor-liquid mixture, at high temperature. These chambers hold a fluid content that is ideally kept at constant condition in pressure and temperature. The pressure difference is maintained between the cold and hot chambers with a pump. The third reactant chamber, which holds the sample vessels, receives the working vapor or vapor-liquid mixture from hot chamber during heating. To cool the reactant chamber, it vents the refrigerant into the low-pressure chamber. The shuttling of vapor or vapor-liquid mixture is controlled via two interconnecting mechanical one-way or two-way valves. One valve interconnects hot to reactant chamber. Another valve interconnects cold to reactant chamber. The working vapor or vapor-liquid mixture is passed between the three chambers via pressure difference between the fluid-holding cold, hot and reactant chambers.

In some embodiments, the thermal cycler device comprises an electrical, compressed air or another type of mechanical pump that does not interconnect the cold and hot chambers. The pump pulls a vacuum on the cold tank and is vented to the outside. Another mechanism of replenishing the escaped water vapor into hot chamber is incorporated into the device in this configuration.

In some embodiments, one hot chamber is used to reduce the number of necessary components of the thermal cycler. The cold chamber is obviated and replaced by a passive pump driven by compressed air. No mechanical pump is needed in this case. Instead, the hot chamber and the passive pump regulate the working fluid phase change independently.

In some embodiments, the pressure or temperature is altered inside the reactant chamber directly without both cold and hot chambers. Instead, an embedded resister heater inside the working chamber heats the working fluid directly. In various aspects, heating may be accomplished using a pump connected directly to the reactant chamber. The pump increases the working refrigerant pressure and therefore the temperature within the reactant chamber during pump up. To cool the working refrigerant inside reactant chamber, the same pump can be reversed to draw the refrigerant vapor out of the chamber during pump down. In this configuration, a single working chamber can be used to further simplify one or more embodiments.

In some embodiments, the systems, devices, and methods comprise a number of distinguishing features, including, but not limited to: utilizing high heat transfer rates of boiling/evaporation and condensation to achieve high thermal cycling rates and temperature uniformity; using the high heat of vaporization to minimize total fluid transport; employing near-reversible cycles with thermal storage chambers for excellent efficiency; and eliminating a substrate holder for reduced mass and raw material cost. A further advantage provided by embodiments of the systems, devices, and method described herein include provision of smaller, faster thermal cyclers that can provide thermal cycling to a plurality of fluid samples in parallel. These and other advantages of one or more aspects will become apparent from a consideration of the ensuing description and accompanying drawings.

BRIEF DESCRIPTION OF THE DRAWINGS - REFERENCE NUMERALS

| Part Number | Part Name |
| --- | --- |
| 100 | housing |
| 102 | lid |
| 104 | holder |
| 106 | sample |
| 108 | wells |
| 110 | cold device |
| 112 | cold chamber |
| 114 | hot device |
| 116 | hot chamber |
| 118 | heater element |
| 300 | sample |
| 302 | working chamber |
| 304 | cold chamber |
| 306 | hot chamber |
| 308 | cold valve |
| 310 | hot valve |
| 312 | inline pump |
| 314 | working fluid |
| 316 | cold fluid |
| 318 | hot fluid |
| 320 | heater |
| 400 | holes |
| 402 | chamber wick |
| 404 | valve connections |
| 500 | sample vessel |
| 502 | ring seal |
| 506 | biomaterial |
| 508 | sample wick |
| 602 | check valve |
| 604 | venturi pump |
| 606 | separator filter |
| 608 | phase separator |
| 610 | fast valve |
| 700 | work chamber heater |
| 702 | work chamber heater wick |
| 704 | flow control device |

DETAILED DESCRIPTION

Certain illustrative embodiments of the systems, devices, and methods are described below. The invention is not limited to these particular, illustrative embodiments. For example, where the description describes "an embodiment" or "one embodiments" or specifies that a particular feature "should" have certain parameters or criteria, it should be understood that such features are not requirements of the invention—but simply illustrative embodiments.

As shown in the drawings for the purposes of illustration, the systems, devices, and methods may be embodied in methods and hardware systems for thermal cycling using phase changing fluids. Embodiments of the invention are useful for rapid, uniform and accurate thermal cycling.

The use of the singular includes the plural unless specifically stated otherwise. Further, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Wherever possible, the same reference numbers will be used throughout the drawings to refer to the same or like parts.

Figure 1A:
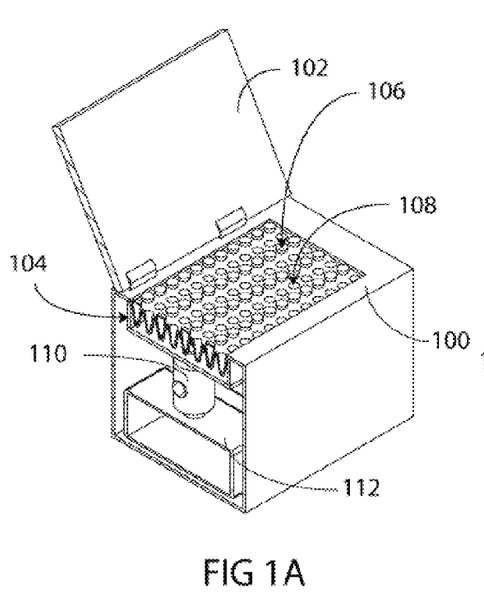
FIGS. 1A and 1B depict perspective sectional views of a thermal cycler in accordance with one embodiment of the invention.
Figure 1B:
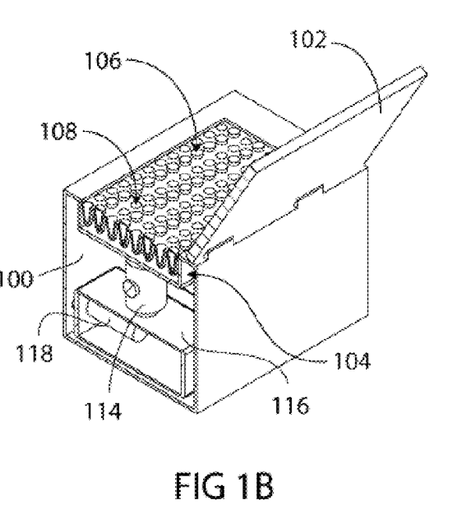

FIGS. 1A and 1B

FIGS. 1A and 1B show perspective sectional views of one embodiment of the thermal cycler. Specifying FIG. 1A is the left-side and FIG. 1B is the right-side view. Referring to FIGS. 1A and 1B, the schematic includes an outer enclosure or housing 100 and a lid 102. Inside enclosure 100, a working chamber 104 has a topside surface adapted to have a plurality of opening or wells 108. The wells are adapted to fit one or more analyte containers, materials or samples 106. The samples conform or makes contact to the inside surface of wells 108. From the bottom surface of holder 104, it comprises a flow control device 110 that connects to a thermal reservoir or chamber 112. Also attached to the bottom surface of holder 104 is a flow control device 114 that connects to a thermal reservoir or chamber 116. A heat generation element or device 118 is mounted to chamber 116.

FIG. 2

Figure 2:
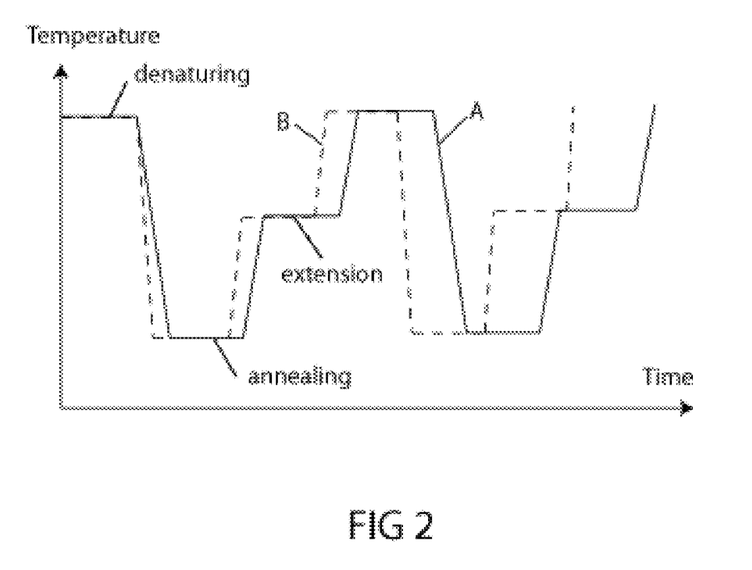
FIG. 2 is a plot depicting the thermal cycling temperature profile as a function of time in accordance with an embodiment of the invention.

FIG. 2 shows a diagram depicting one example for a temperature profile of conducting or operating PCR, LDR or other temperature cycling processes. These procedures provide the method of duplicating or amplifying genetic material or heating and cooling other chemical or biological substance. In various aspects, the PCR process is conducted on analyte samples 106 that may contain genetic material, e.g. DNA segments or strands, primers and polymerase molecules. The PCR process comprises a number of cycles. Typically, one cycle comprises three steps, e.g., denaturing, annealing, extension, each corresponding at a particular temperature (although fewer or greater numbers of steps may be employed). These holding temperatures may occur at 90 to 95° C. in the denaturing stage, 55 to 50° C. in annealing stage, and 70 to 75° C. in the extension stage. In another example, a cycle comprises two temperature stages, one corresponding to denaturing and the other to annealing and extension. The first stage may occur at 90 to 95° C. and the second stage at 50 to 70° C. In a PCR process, it can take up to a total of 50 cycles to complete, although fewer and greater numbers of cycles are contemplated.

The systems, devices, and methods described herein provide a thermal cycling method for conducting PCR that is faster, more uniform, and more accurate than previously available approaches. For example, the thermal cycling speed is measured by the change of temperature per unit time, e.g. 1° C./s, on average for a plurality of analytes samples. In another example, referring to FIG. 2, a faster overall thermal cycling is to reduce the time during temperature ramping. In this case, cycle B is faster than cycle A due to faster temperature ramping between each denaturing, annealing and extension stage. Also, temperature uniformity is measured by the temperature difference between two or more samples during any PCR stages. For example, during the extension reaction at constant temperature, sample-to-sample temperature variation may be quantified by 1° C. Another metric for improvement over prior approaches is temperature accuracy. It refers the difference between the specified and actual temperature of samples 106 during thermal cycling. For examples, a measurement of 1° C. can account for any undershoot or overshoot that may occur at the end of each heating and cooling stage.

FIG. 3

Figure 3:
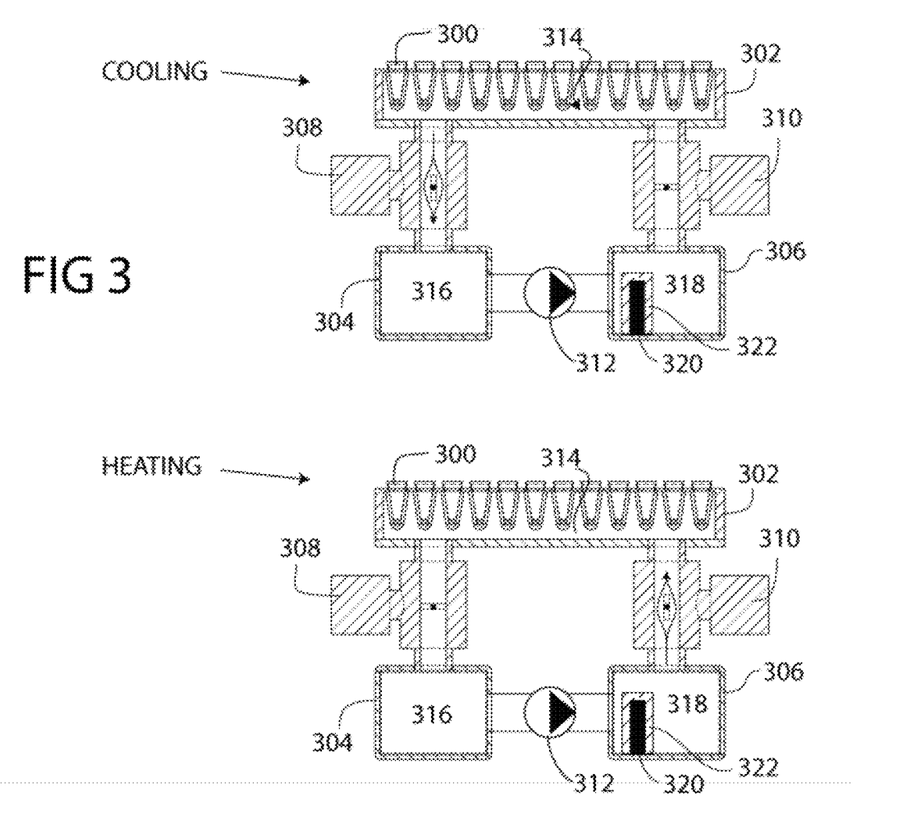
FIG. 3 is a schematic showing sectional views of a thermal cycler in accordance with an embodiment of the invention.

Referring to FIG. 3, the schematic of one or more embodiments includes analyte samples, solutions, or mixtures 300 that contains genetic materials or other biomolecules. There are three fluid containers, tanks or chambers 302, 304, and 306. Said chambers include a working chamber 302, a hot chamber 306, and a cold chamber 304. Each said chamber contains the vapor or vapor-liquid mixture of a chosen fluid 314, 316, and 318 that are identical in chemical composition. In some embodiments, the said fluids have different thermodynamic properties. Namely, a hot fluid 318 fills chamber 306; a cold fluid 316 fills chamber 304; and a working fluid 314 fills chamber 302. Moreover, chamber 302 has an upper surface that comprises opening or wells adapted to fit a plurality of samples 300. A cold valve 308 interconnects chambers 302 and 304 and a hot valve 310 interconnects chambers 302 and 306. An electrical filament, resistor, element or heater 320 is provided. A mechanical or electrical pump or compressor 312 interconnects chambers 304, 306.

In more detail, referring to FIG. 3, sample 300 comprises a liquid inside a vessel with a cap or lid that can be opened and closed. Further description on sample 300 is disclosed in reference to FIGS. 5A and 5B. Also, the walls of the chambers 302, 304, and 306 may be insulated for heat retention and prevent heat transfer to and from the surrounding. The conditions of the refrigerant vapors or vapor-liquid mixtures 314, 316, and 318 are as follows. Inside chamber 306, the hot refrigerant vapor or liquid-vapor mixture 318 is kept at substantially high pressures and temperatures. Cold chamber 304 contains the cold refrigerant vapor or liquid-vapor mixture 316 at substantially low pressure and temperature. Inside chamber 302, fluid 314 can have temperature and pressure in between fluids 316 and 318. The compressor 312 provides the means to maintain the aforementioned pressure and temperature difference between the hot and cold chambers.

In further detail, inside chamber 302, the working fluid 314 has pressures lower than fluid 318 but has higher pressure than fluid 316. The said fluids are either at or near saturation, in reference to the thermodynamic property of a fluid substance. Similarly, the pressure and temperature of fluids 314, 316, 318 are given by its saturation data and not allowed to vary independently. Henceforth, the terminology 'fluid' is used interchangeably with saturated or superheated vapor, saturated or undercooled/supercooled liquid, or a mixture of vapor and liquid. All three fluids 314, 316, and 318 are the same substance in this embodiment. The hot and cold chambers 316 and 318 can be considered as mechanisms of providing thermal reservoirs or storage. That is, the hot refrigerant 318 and cold refrigerant 316 are intended to have constant or near constant temperatures and pressures during PCR operation. The interconnecting cold and hot valves 308,310 are responsible for venting fluids in chamber 306 into chamber 302 and in chamber 302 into 304. Valves 308 and 310 can operate pneumatically or electronically or by any other desired mechanism.

In further detail, still referring of FIG. 3, the chosen hardware specifications should satisfy the design of one or more embodiments. The reactant chamber 302 is sufficiently wide (W), long (L) and tall (H) to secure and seal the samples 300 in place. Chamber 302 may have outer dimensions 5" by 6" by 1" (Width×Length×Height) to hold ninety-six or any substantial number of analyte samples 300. The size of the chambers 304 and 306 is sufficiently wide, long and tall so that the temperature and pressure of the conditions inside the chambers does not vary significantly (e.g., 5 percent or less) over the entire PCR process. Chambers 304 and 306 may have outer dimensions measure 6" by 6" by 5" (W×L×H). Also, chambers 302, 304, and 306 should have walls thick or rigid enough to withstand the operating pressures inside each said chambers. The walls of chambers 302, 304, and 306 may also provide thermal insulation to reduce parasitic thermal loss. Valves 308 and 310 are sufficiently large, measured in terms of maximum pressure rating and flow coefficient, to allow rapid venting of the vapor between chambers 314, 316, and 318. Vapor flow rate is typically measured in mass flow per unit time. The proper valves to use typically balance the trade-off between valve size, flow rate and speed.

The construction of one or more embodiments is as follows. The placement of chamber 302 is such that the loading and unloading of samples 300 is easily accessible by anyone using the thermal cycler. Chambers 304 and 306 should be placed as close to chamber 302 to prevent heat loss. Chambers 304 and 306 can be arranged side by side next to chamber 302 or stacked below chamber 302. The connection between pump 312 and chambers 304 and 306 can be hermetically threaded or welded connections to prevent leakage. A typical connection should withstand up to 100 psi in gauge pressure. The connection points need not to be at the bottom of the chambers 302 as shown in the schematic. The connection of pump 312 should be chosen to allow only vapor passage in one or more embodiments or only liquid passage in other embodiments, depending on the type of pump 312. Inside chambers 304, 306, the condensed liquids tend to settle at the bottom of said chambers.

Still referring to FIG. 3, the chosen fluid 314, 316, and 318 should satisfy these conditions in one or more embodiments. Its boiling point, as defined by the temperature at which the liquid phase becomes its vapor at one atmosphere pressure, or about 15.7 psi, should be below or near the temperatures during denaturing stages (~95° C.). The said refrigerant should have a saturation pressure at the annealing temperature (~45° C.) that is easily obtainable by conventional pumps or pump systems (for example, 28 psi gauge pressure of vacuum). The said refrigerant should have a high latent heat, or the heat of vaporization, compared to other available refrigerant fluids. Incondensable gas species should not contaminate the working fluid more than 20% by molarity.

The construction material of chambers 302, 304, and 306 should be rigid and strong to withstand or maintain their shape against positive and negative pressure difference, e.g., gauge pressure, measured against atmosphere. A few of the many possible materials are stainless steel, plastics, plastic composites, or other materials that has a Young's modulus greater than ~50 GPa. The said materials should also protect against corrosion or scaling to maximize device life. These features may be attained with the correct material or via applying passivation coatings. The walls of chambers 302, 304, and 306 can also be filled with insulting materials such as foam or other low thermal conductance material. The walls may also be evacuated as a means of forming a vacuum inside for heat retention. The chosen construction methods and component dimensions should maximize thermal insulation against heat loss to the surrounding while minimizing built cost.

Valves 308 and 310 can be a pneumatic, compressed air, or a solenoid valve, or any other desired mechanism. It should be made of a material that matches chamber 302, 304, and 306. Said valves can be attached to chambers 302, 304, and 306 either with threaded or welded connections. The said connection should prevent fluid leakage under positive or negative gauge pressures up to ~250 psi gauge pressure. Valves 308 and 310 should also be able to quickly open and close with substantially precise timing as to allow a predetermined amount of vapor to pass through (e.g. 1-10 Hz with 10% accuracy). The duration of the opening for valves 308 and 310 is typically 0.001-0.1 second to allow precise heating and cooling control. Valves seals should use a material able to withstand the highest temperature reached by the hot chamber 306 (e.g., stable up to 350° C. such as fluoroelastomer, silicone, PTFE or other compounds). The valve seals should also be chemically compatible, e.g. no degradation over time, to the chosen working fluid.

Heater 320 provides substantial heating within chamber 306 to rapidly increase the temperature of its containing vessel or chamber. Heater 320 is made with an electrically conductive material. Its composition may comprise or consist of nickel-chromium alloy, iron-chromium-aluminum, or nickel-iron with various elemental concentrations that is resistant to corrosion or thermal oxidation. The chosen material, if provided without insulation, should be compatible with working fluids 314, 316, and 318. A heat resistant metal or plastic envelope 322, e.g. laminated polymer or Kaplan, may enclose or wrap heater 320 to extend it operational life. In various embodiments, heater 320 is surrounded by an envelope made from an open, porous structure. The structure may retain the condensed fluid 318 in the pores thereof near or at the heater 320 interface. In various embodiments, heater 320 is a filament or cartridge type imbedded into the walls of chamber 306. The wire gauge, e.g., its diameter, may be chosen from 18 to 30 (0.25 to 1.02 mm) to maximize heating power and durability. In various aspects, thermal paste or pad is used as a mechanism to improve heat transfer between heater 320 and chamber 306. In various aspects, heater 320 may be placed inside chamber 302 without forming thermal contact to said chamber. Here, heater 320 may be attached to the wall of chamber 306 by threading or chemical bonding. Any combination of the aforementioned types, material or configuration may be used to provide rapid heating to fluid 318.

Compressor 312 can be pneumatically, compressed air, or electrically operated or by any other desired mechanism. The compressor type can be reciprocating or rotary. The compressor should be semi-hermetic, hermetic, or welded at all metal joints to prevent leakage and contamination. The said compressor should be substantially powerful (0.01-1 hp) so that it can maintain a large pressure difference (>50 psi). The said compressor should also have adequate flow rates so that the pressure and temperature of fluids 316 and 318 do not vary significantly (<5%) over the entire PCR process. More powerful compressors (>1 hp) maybe used in one or more embodiments where two or more working chambers 302 are connected to chamber 306, 308. The rated power of pump 312 should supply a substantial pressure difference between fluids 316 and 318.

Still referring to FIG. 3, the schematics describe one embodiment of the thermal cycling method. Referring to FIG. 3A (top image), the procedure for cooling the working fluid 314 is described as follows. Valve 310 is now closed. A vacuum, e.g., negative gauge pressure, is maintaining by pump 312 for fluid 316. Said fluid has a lower pressure than fluid 314. To cool fluid 314, valve 308 opens to vent the high-pressure fluid 314, into chamber 304. As this occurs, both fluid pressure and temperature inside chamber 302 will fall due to the evaporation of fluid 314. The desired amount of cooling, as given by the total temperature fall of fluid 314, is controlled by the opening duration of valve 308. As a result of cooling the fluid 314, the analyte samples 300 will also become cooler via thermal conduction across the wall of sample vessel 300. In one or more aspects, the said valve is controlled electronically and can open and close with frequencies up to 1000 cycles/second or Hz. The high rate of actuation can, in some aspects, improve the control of the vapor vented into chamber 316

Referring to FIG. 3, the procedure for heating the refrigerant 314 is described as follows. Valve 308 is now closed. A positive gauge pressure is maintained by pump 312 for the hot refrigerant 318. Said fluid has a higher pressure than fluid 314. To heat fluid 314, valve 310 opens and vents the hot fluid 318 into chamber 302. As this occurs, both fluid pressure and temperature in chamber 302 will rise as fluid condensation occurs on the walls of said chamber and samples 300. The desired amount of heating, as given by the total temperature increase of fluid 314, is controlled by the opening duration of valve 310. As a result of heating the fluid 314, the analyte samples 300 will also become hotter. This heating process occurs through thermal conduction across the vessel wall 300.

Still referring to FIG. 3, PCR may be performed using the thermal cycler in one or more manners as described below. Initially, a PCR user may load or seal up to 96 or more analyte samples into chamber 302. Then, pump 312 is turned on to transfer fluids in chamber 304 into chamber 306. Subsequently, a pressure difference will build up between fluids 316 and 318. If the walls of chambers 304 and 306 were thermally insulated, a temperature difference will also be maintained between fluids 316 and 318. In approximately 1-5 minutes, the steady-state temperature and pressure would be reached. An example of the fluid property is about 95 C and 22 psi (absolute pressure) in chamber 306 and about 55 C and 1.5 psi (absolute pressure). These values are related to the saturation condition of the working fluid.

After the system initializes by reaching steady state in fluids 316 and 318, the thermal cycling may start heating the analyte samples 300 to the denaturing stage (between 90 to 95° C.). To heat, valve 310 is opened. In one or more aspects, the valve 310 is opened for 1 second and is controlled electronically. Valve 310 may open and close with frequencies up to 1000 cycles/second or Hz. The high actuation rate of said valve can, in some aspects, improve the control of the vapor flow into chamber 302. This provides the means of controlling the pressure of fluid 314 inside chamber 302. In further detail, fluid 318 is a saturated or superheated vapor, e.g. water vapor, and would thereby condense as said fluid vapor enters chamber 302. The condensation will occur at the surface of chamber 306 and sample 300. This process provides the means of heating, or transferring thermal energy, into sample 300. In various embodiments, the final temperature of the sample 300 is the temperature needed for the denaturing stage.

After the denaturing stage, in connection with FIG. 3, the analyte samples 300 should be cooled to the annealing temperature (between 50 to 55° C.) or, in other methods, the annealing/extension temperature (between 50 to 65° C.). To cool, valve 308 opens briefly. In other cases where fluid 314 is a saturated or a vapor/liquid mixture, the vapor will vent into chamber 304. As pressure falls in chamber 302, the liquid will evaporate and cool to a lower temperature. Consequently, the samples 300 are then cooled by heat loss through the wall 300. The cooling process is called evaporative cooling. It is controlled by the opening time of valve 308.

In various PCR methods, after the annealing stage, the samples 300 should be heated to the extension stage (between 70 to 75° C.) to complete one cycle of DNA replication. Here, the same procedure for heating to the denaturing stage may be used. A smaller temperature increase of fluid 314 is controlled by a shorter opening time of valve 310. Once the required temperature is reached, samples 300 will undergo the chemical changes to complete one full cycle of denaturing, annealing, and extension steps. Subsequent cycles may be accomplished by repeating the above heating and cooling procedure.

In various aspects, referring to FIG. 3, the cooling rate can exceed 30° C./sec for samples 300 between the various constant temperature stages. Also, a temperature uniformity of <0.1° C. maintained and a temperature accuracy <0.5° C. are kept amongst said samples.

Figure 4A:
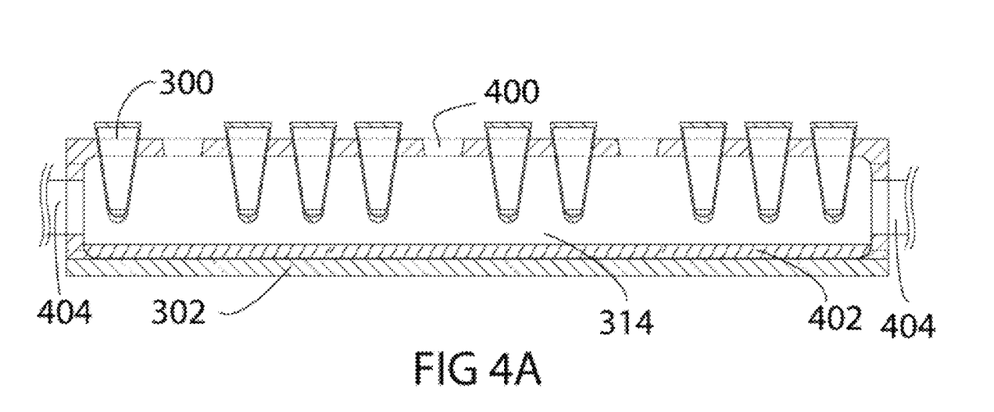
FIGS. 4A and 4B are schematics depicting sectional views of the working chamber in accordance with an embodiment of the invention.
Figure 4B:
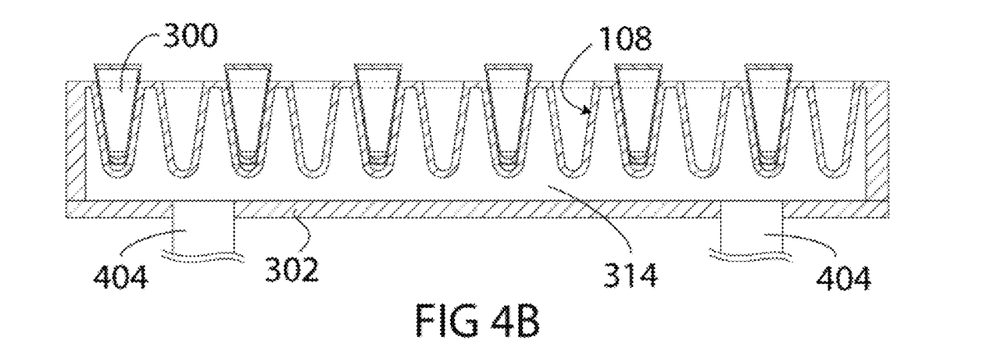

FIGS. 4A and 4B

FIGS. 4A and 4B illustrate additional embodiments of the working chamber 302. Referring to FIG. 4A, chamber 302 comprises retaining holes or openings 400 adapted to fit a plurality of samples 300. Here, the samples directly contact the fluid 314 during thermal cycling. In various aspects, the advantage is to provide the highest heating and cooling rates for samples 300. In various aspects, the total number of samples undergoing PCR is less than the number of openings 400. Dummy sample vessels (not shown) are used in place of otherwise empty openings 400. In some embodiments, the internal surfaces of chamber 302 are partially or fully covered by an opened structure foam, wire screen, or wick 402. The function of said wick is to provide a structure that retains and distributes the condensed liquid of fluid 314. This provides the means to overcome issues such as non-uniform temperature distribution within chamber 302. Also, the said wick provides the nucleation sites of the condensation or evaporation processes during heating and cooling, respectively. One advantage is to improve the temperature uniformity (to within 0.1° C.) within chamber 302. Another advantage is to prevent dry-out conditions during cooling. Dry-out occurs during evaporation when a particular surface area becomes dry and can no longer create the associated cooling effect. In various embodiments, a separate holding tank (not shown) may contain working fluid liquid that is placed inside or outside chamber 302. The extra liquid will then supply liquid to wick 402 by capillary forces or gravity.

The average pore size of the open structure wick 402 is in general less than one hundred micrometers to be effective. The overall thickness of said wick is substantial to avoid dry-out, which is typically between 0.1 and 5 millimeters thick. The said wick material may be ceramic, plastic, metallic, or a combination of all three. The wick material may be inherently hydrophilic or it may consist a surface treatment, e.g. hydrophilic coating, to maximize liquid transport. The wick 402 material may also consist of oxidized copper or aluminum screen or cloth that has mesh sizes larger than 100×100 or opening widths less than 200 micrometers. The wick 402 may comprise a composite made up of different materials as such ceramic, plastic and metal to maximize fluid transport. The wick surface coverage of chambers may be non-uniform or spotty to maximize vapor transport during boiling/evaporation.

Referring to FIG. 4B, chamber 302 comprises closed wells 108 adapted to fit a plurality of samples 300. Here, the samples, partitioned by the wall of chamber 302, do not directly contact fluid 314. Instead, the wall of the chamber 302 separates samples 300 from fluid 314 during thermal cycling. The advantage is to prevent contamination to either fluid 314 or the sample 300. In various aspects, it is useful to prevent contamination to fluid 314. Maintaining constant chemical composition of fluid 314 provides a mechanism to keep its thermodynamic properties constant. The substantially saturated fluids ideally provide the highest heat transfer rates from the chamber wall to said samples. In various embodiments, the internal surfaces of chamber 302 may be partially or entirely covered by wick 402 as described in reference to FIG. 4A.

Referring to FIGS. 4A and 4B, fluid 314 vapor is designed to pass through threaded or welded connections 404 to and from interconnecting valves (not shown). The placement of connections 404 may be optionally located at either the bottom or the sides of chamber 302. In some embodiments, a substantial number of connections 404 may be provided to improve fluid transport uniformity and speed during temperature cycling. To further improve transport, gas manifolds may be constructed into the working chamber, whose advantages are to reduce drag and increase gas flow efficiency of the working fluid 314.

Referring to FIGS. 4A and 4B, additional embodiments of the wall of chamber 304 may include conformal contours to the shape of the analyte samples 300. In one or more aspects, the clearance gap between said vessels and the bottom wall of chamber 302 is between 1 to 10 mm. Smaller clearances reduce the required volume of vapor needed to fill the inner cavity of chamber 302. This reduces the fluid volume needed and improves the overall thermal cycling speed. In contrast, thicker clearances allow more efficient fluid transport. In one or more aspects, the clearance gap maximizes fluid flow transport and minimizes the void volume within chamber 302.

Figures 5A, 5B:
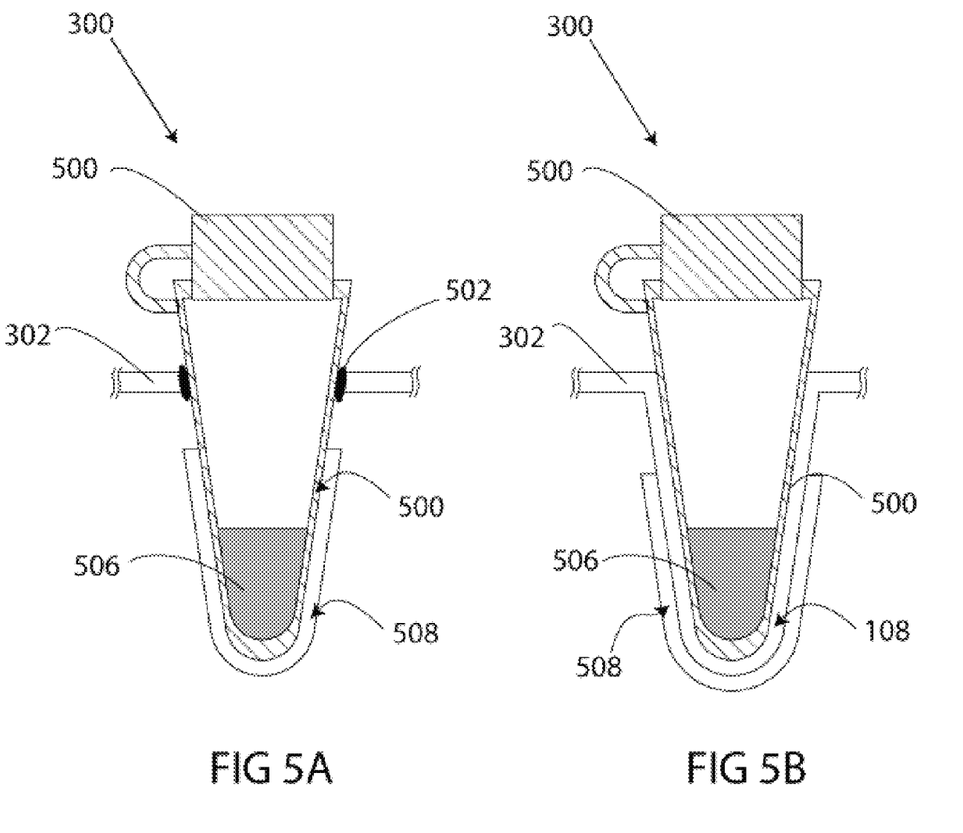
FIGS. 5A and 5B are schematics depicting sectional views of the analyte sample in accordance with an embodiment of the invention.

FIGS. 5A and 5B

In FIGS. 5A and 5B, there is shown schematics of one or more embodiments of sample 300 as depicted in FIGS. 1 and 3. Referring to FIG. 5A, chamber 302 comprises a plurality of openings that hold one or more analyte samples 300. In more detail, the sample 300 comprises of a hollow envelope, container, or vessel 500. The wall of vessel 500 can be made up of plastic, stainless steel, or other biocompatible materials, and can have a sealable lid. Inside said vessel, an analyte liquid 506 may contain genetic material or other temperature sensitive substance dispersed within a soluble liquid such as water or saline solution. In various embodiments, the volume of the analyte liquid 506 used in gene replication and detection can range from one-tenth to one hundred microliters. Moreover, sample 300 is held in place securely by a flexible ring or seal 502 into the wall of chamber 302 to prevent fluid leakage. Seal 502 may comprise rubber or other high-temperature tolerant elastomers.

Still referring to FIG. 5A, a porous foam, screen or wick 508 is attached to the external surface of vessel 300. Wick 508 has similar material properties as wick 402. One advantage of the wick 508 is to extend the effective surface area of the sample vessel 300 and enhance heat transfer rates. The open structure of wick 508 also helps to retain the condensed liquid at the surface of the sample vessels 300 during heating. This is desirable because the saturated liquid inside said wick provides the cooling effect during boiling/evaporation.

Now referring to FIG. 5B, chamber 302 comprises a plurality of wells 108 that fits one or more samples 300 as described in reference to FIG. 4B. The wells have outward-facing surfaces that fully contacts sample 300. For the inward-facing surface, which also forms the internal wall of chamber 302, wells 108 is adapted with wick 508 to provide the advantages of said wick as described in reference to FIG. 5A. During operation, the working fluid shuttled in and out of chamber 302 does not contact the walls of samples 302. This provides the means, in reference to FIG. 5B, to eliminate the possibility of cross-contamination with device internals.

FIG. 6

Figure 6:
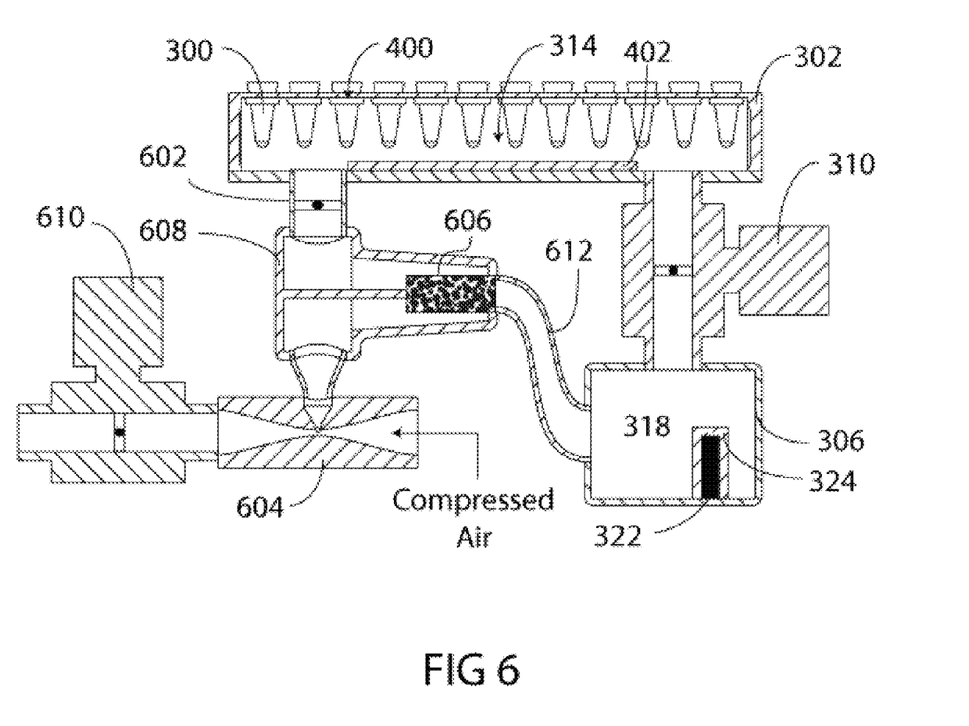
FIG. 6 is a schematic depicting a sectional view of a thermal cycler in accordance with an embodiment of the invention.

FIG. 6 illustrates a sectional view of the PCR thermal cycler of additional embodiments. In addition to previously mentioned components, the thermal cycler comprises other elements that include an electronic, pneumatic, or mechanical valve 602 attached to chamber 302. Attached to valve 602 is an air-liquid or two-phase separator 608. Separator 608 comprises a liquid-capturing material, wick or filter 606 for trapping and holding the liquid refrigerant that had vented from chamber 302. Separator 608 can have two or more ports, where one port connects to an in-line vacuum pump 604. Another port of separator 608 leads to chamber 306. For pump 604, it has a total of 3 or more ports. In various embodiments, one port is connected to a compressed air source. In one or more aspect, a remote or decentralized pump may supply the compressed air source. The other port of pump 604 is connected to an electrical or pneumatic valve 610. Said valve is opened to the atmosphere. In various embodiments, all joints may be threaded, welded or a combination of both to minimize or prevent fluid leakage.

Continuing, in various embodiments, the placement of elements 602, 604, 608, and 610 is not limited by the configuration as it appears in FIG. 6. In one or more aspects, the air-liquid separator may be placed between valve 610 and pump 604. In various embodiments, valve 610 is placed at, near, or integrated with any one or more ports of pump 604. In various embodiments, addition electronic or mechanical valves 610 can be included in the configuration for additional flow control. In various embodiments, multiple vacuum pumps 604 may provide the means to create vacuum in chamber 302. The said pumps may be configured in series or in parallel with respect to the flow paths of the working fluid exiting from valve 602. In various embodiments, fluid tubing 612 may have multiple branches that connect between chamber 306 and separator 608. In various embodiments, the said branching may also be used for connecting multiple separators 608 and valve 610.

In more detail, still referring to FIG. 6, component material and dimension specifications are described as follows. In various aspects, valve 602 is electronically or mechanically controlled. The said valve can be actively or passively operated by which, in the former, electrical, pneumatic or mechanical energy is applied to said valve, or, in the latter, said valve is operated purely by the pressure difference on either side of said valve. In the former, valve 602 is a solenoid or pneumatic type, and in the latter said valve is a one-way check valve. Next, vacuum pump 604 may operate by the Venturi effect, whose type is also known as a jet or an ejector pump. In various aspects, the said pump as an assembly may have integrated elements that include a blow-off mechanism, pressure/temperature/flow sensors, flow control, air manifolds, and thread fitting adapters. These elements allow the pump assembly to reduce wiring/plumbing, input air, and difficulties in integration. Next, the compressed air supply may have pressures in the range of 10-300 psi. The said supply may comprise air, oxygen, nitrogen, or other elemental composition or mixtures that do not condense, e.g. liquefy or solidify, in standard temperature and pressure (STP) conditions. Next, valve 610 is a solenoid or pneumatic type. In various embodiments, the said valve may be connected to separator 608 or to pump 604 to control the flow rate of gas, liquid or a mixture of both. In various aspects, the flow rate is regulated between 0.1 to 100 cubic-foot per minute.

Still referring to FIG. 6, exemplary size and material specifications are described as follows. In various embodiments, valve 602 is a one-way check valve oriented to allow flow to exit chamber 302. The outer dimension of valve 602 may be 2" by 1" by 1" (W×L×H). In various aspects, the valve 602 body may be constructed out of brass, steel, or stainless steel, optimized for cost, durability, corrosion control and strength. The seals within said valve are made with fluoroelastomer, silicone, PTFE or other metal or plastic materials, chosen to withstand the pressure and temperature range of the working fluid 314. Pump 604 body may be constructed using brass, stainless steel, or aluminum, and may have outer dimensions of 5" by 1" by 1" (W×L×H). The said pump may be of single stage, or multistage type. Next, tubing 612 may consist of various plastics or metals, including fluoroelastomer, silicone, PTFE, brass or steel that can withstand the temperature range of working fluid 314. The outer diameter of said tubing may be between ½" to 3". In various aspects, line or tubing 612 may be braided with metal sheathing to maintain pressure and prevent contraction or expansion of said line or tubing. In various embodiments, filter or wick material, which has fine open or closed pores between 0.1 to 100 micrometers, is integrated into tubing 612 to control the flow rates of liquid or gas. Next, in various embodiments, the air-liquid separator 608 may be a liquid wick enclosed within a plastic or metal casing. Wick material may be porous plastic (e.g., polytetrafluoroethylene (PTFT), polyethylene, polypropylene or glass) or porous metal (e.g., sintered copper powder or copper mesh screens). The other casing of separator 608 may be plastic or metal of similar or exact materials as previously mentioned. Similar materials as described for valve 602 can make the seal and body of valve 610. In various aspects, the said valve may 2-way or 3-way as a means to provide substantial flow rates and simplify plumbing.

Still referring to FIG. 6, exemplary operational specifications of the thermal cycling process during PCR are described in detail. Specifically, in one or more embodiments, the PCR process is conducted through rapid, accurate and uniform heating and cooling stages for a plurality of samples 300. In various aspects, the PCR process follows one or more combinations of constant temperature stages consisting of annealing (between 55 and 60° C.), annealing/extension (between 60 and 65° C.), melting or denaturing (between 85 and 98° C.), and extension (between 70 and 75° C.).

The procedure for cooling the working fluid 314 is described first as follows. In various embodiments, a negative or vacuum pressure is generated by pump 604 and driven by compressed air. Now, valve 610 opens with a predetermined duration and frequency to allow the compressed gas to flow through pump 604. With minimum time delay, a vacuum pressure is created at the inlet port of pump 604 with a value lower than that inside chamber 302. Concurrently, valve 602 opens to vent the pressurized fluid inside chamber 302. In various aspects, valve 602 is a check valve and said valve opens when the downstream pressure drops below the upstream pressure. In various aspects, where an electronic or pneumatic valve is used, an external electrical signal would actuate the opening and closing of valve 602. As fluid vents, both pressure and temperature inside chamber 302 will fall in accordingly to saturation properties of the working fluid 314. During venting, fluid evaporation occurs within chamber 302. For the forgoing cooling process, in various aspects, the desired amount of cooling, as given by the temperature reduction of fluid 314, is controlled by the opening frequency or duration of valve 602. In various aspects, the same cooling phenomenon is controlled by the opening frequency or duration of valve 610. In various embodiments, after the desired cold temperature is reached in chamber 302, valve 610 closes and the compressed air pushes valve 602 close. In various aspects, temperature of fluid 306 is tracked in real-time and valve 602 may be actuated open briefly to maintain the desired temperature. In various aspects, both temperature and pressure are measured inside chamber 302 using thermocouple probes and pressure transducers. As a result of cooling the fluid 314, the analyte samples 300 will be cooled due to thermal conduction across the vessel wall 300. In some aspects, the minute amounts of analyte solution inside sample 300 will equate quickly in temperature with a colder fluid 314.

Still referring to FIG. 6, the component operational specifications are described in detail. Valves 602 and 610 are sufficiently large, measured in terms of maximum pressure rating and flow coefficient, to allow rapid venting of the vapor, liquid or a mixture of both. Valves 610 should also be able to quickly open and close with a substantially precise timing as to allow a predetermined amount of vapor to pass through (e.g. 10-1000 Hz with 10% accuracy). In various aspects, the duration of the opening for valves 610 is between one hundred microseconds to seconds. Vapor flow rate is typically measure in mass flow per unit time. In various aspects, the maximum rated flow rate for valve 610 is inversely related the maximum rated speed of opening/closing. The proper valve selection should balance the trade-off between valve size and speed. Next, the vacuum pump 604 is sufficiently large, measured in terms of maximum flow rate and maximum vacuum pressure, to provide substantial speeds in creating the required vacuum pressure (e.g., from 5 to 28 in-Hg) in chamber 302. In various aspects, the time needed to reach 28 in-Hg of vacuum pressure from STP is 0.1 second. In various aspects, the said pump uses relatively low amounts of pressurized gas source, e.g., 1:1 ratio between the two volumetric flow rates, to reduce energy consumption. Next, separator 608 should be sufficiently large, measured by pressure drop within its range of flow rates, to provide substantial flow so that the said separator does not limit the performance of components 602,604, and 610. Last, the fluid tubing 612 should be sufficiently strong to prevent deformation or rupture for pressures rated up to 200 psi and temperatures up to 300° C.

Still referring to FIG. 6, the liquid return process is described as follows. In various embodiments, the fluid 314 exiting valve 602 has a lower pressure and temperature than the fluid inside chamber 302. The low pressure is generated by pump 604, driven by the compressed air source. At the inlet port of separator 602, a fluid mixture is formed whose composition comprises the compressed gas and the working fluid species. In various aspects where pump 604 is connected between valve 602 and separator 608, the mixing process inside said pump allows the work fluid to condense completely. Then, once the fluid mixture reaches inside the air-liquid separator, the liquid is trapped by filter 606 and gas species exits into the atmosphere. In various aspects, valves 602 and 610 both closes, e.g. during heating, allowing the stored liquid to pumped back into chamber 306 by the compressed air.

Referring to FIG. 6, the procedure for heating the fluid 314 follows the description in reference to FIG. 3. In various embodiments, the pressure and temperature of fluid 318 is raised to predetermined values by the heater 322. In various aspects, temperature and pressure are tracked and maintained inside chamber 306 using sensors, probes, or transducers. Any number of measurement elements can be mounted inside chamber 302, as well as integrated with heater 322. On and off signals can be sent to the heater, via an electrical relay, to adjust the heating power according to real-time measurements.

In various aspects, referring to FIG. 6, a heating rate can exceed 30° C./sec for samples 300, temperature uniformity <0.1° C. maintained between the plurality of said samples, and temperature accuracy <0.5° C. kept amongst all of said samples. In various aspects, the starting fluid property is about 55° C. and 1.5 psi (absolute pressure) in chamber 302 at the start and reaches 95° C. and 22 psi (absolute pressure) at the end of heating process. These values and of various embodiments match the saturated condition of the working fluid if either distilled, deionized, or tap water was used. In various aspects, the saturation temperature and pressure would be different for fluids such as methanol, alcohol, fluorinated fluids, or other refrigerants used.

FIG. 7

Figure 7:
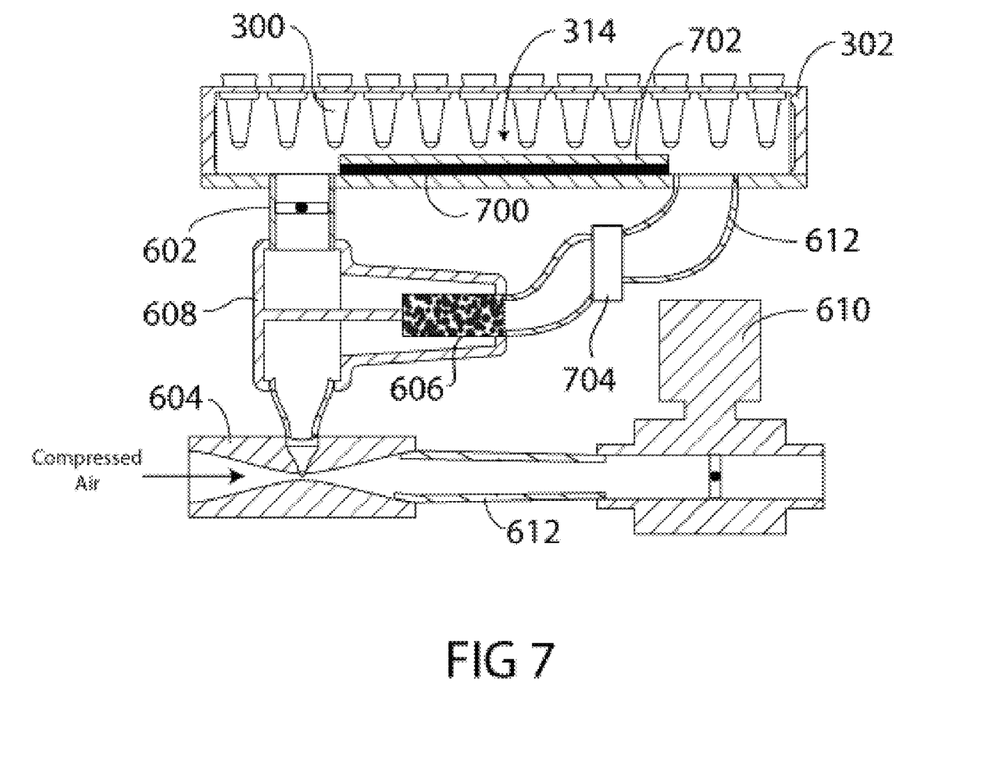
FIG. 7 is a schematic depicting a sectional view of a thermal cycler in accordance with an embodiment of the invention.

FIG. 7 illustrates a sectional view of the PCR thermal cycler of additional embodiments. In addition to components already described, the various embodiments comprise other elements, without limitations on the type, quantities, or material. First, an electrical filament, resistor, element or heater 700 is mounted directly to chamber 302. Next, a plastic or metallic porous media, material or wick 702 is placed in contact to the said heater 700. In various embodiments, an electronic, pneumatic, or mechanical valve 606 is attached to chamber 302. Interconnecting one or more sections of tubing 612 is an electronic or mechanical flow control device 704.

In further detail, still referring to FIG. 7, heater 700 provides substantial heating within chamber 302 to rapidly increase the temperature of samples 300. In various embodiments, heater 700 is a resistive filament or cartridge type imbedded into the walls of chamber 302 in a manner that forms thermal contact with said chamber. In various aspects, thermal paste or pad is used as means to improve heat transfer from heater 700 to chamber 300. In one or more embodiments, heater 700 conforms tightly without spacing to the internal surface contours of chamber 302. The exposed surface of heater 700, in various aspects, may be partially or fully covered by wick 702. The attachment method between heater 700 and chamber 302 may include using glue, tape or other chemical bonding agents. In various aspects, heater 700 may be suspended inside chamber 302 without forming thermal contact to said chamber. Here, heater 700 may be attached to the wall of chamber 302 by threading or chemical bonding. Any combination of the aforementioned types may be used to provide rapid heating to fluid 314.

In reference to FIG. 7, the wick 702 is attached to heater 700 to provide a continuous feed of condensed liquids to the hot surface of said heater. Wick 702 may wrap tightly around heater 700 in a conforming manner that does not break thermal or fluid contact with said heater. Wick 702 may also be placed between heater 700 and the wall of chamber 302. In various aspects, heater 700 is placed between wick 702 and the wall of chamber 302. Wick 702 may or may not be put in thermal contact or fluid contact with wick 308. In various aspects, a porous wick may form any portion of the internal volume of tubing 612. In various embodiments, the control device 704 connects directly to chamber 302 and replaces valve 606 to simplify the overall design. The various embodiments may also operate without device 704. In the absence of said device, the function of modulating liquid flow may be built into the separator 608. In various embodiments, device 704 or separator 608 may be placed or mounted anywhere on the external walls of chamber 302. A plurality of separator 608 may be used to increase the recovery of the condensed liquid that had exited from valve 602. One or more of a plurality of separators 608 may be connected between elements 602 and 604 or between 604 and 610.

In further detail of component specifications, heater 700 is made with an electrically conductive material. Its composition may comprise nickel-chromium alloy, iron-chromium-aluminum, or nickel-iron with various elemental concentrations that is resistant to corrosion or thermal oxidation. The chosen material, if used without insulation, should be compatible with working fluid 314. The filament gauge, e.g. diameter, may be chosen from 18 to 30 (0.25 to 1.02 mm) to maximize heating power and durability. Heat resistant metal or plastic, e.g. laminated polymer or Kaplan, may enclose or wrap heater 700 to extend it operational life. Next, device 704 may be a passive or an active flow control valve. In various aspects, device 704 may open or close at a predetermine pressure differential as a two-way or a one-way check valve. Also, device 704 may open or close using electronic or pneumatic means, e.g. a solenoid or compressed air valve, as a two-way or a one-way (check) valve.

Referring to FIG. 7, exemplary operational specifications of the thermal cycling process during PCR are described in detail. The manner of using the various embodiments starts with loading the samples 300 into chamber 302. Specifically, in one or more embodiments, the PCR process is conducted through rapid, accurate and uniform heating and cooling stages for a plurality of samples 300. In various aspects, the PCR process follows one or more combinations of constant temperature stages consisting of annealing (between 55 and 50° C.), annealing/extension (between 50 and 65° C.), melting or denaturing (between 85 and 98° C.), and extension (between 70 and 75° C.).

Referring to FIG. 7, the procedure for cooling the fluid 314 follows the description in the various embodiments shown in FIG. 7. In reference to FIG. 1, samples 300 are cooled when going from denaturing to annealing. In various aspects, the cooling rate can exceed 30° C./sec for samples 300, temperature uniformity of <0.1° C. maintained between the plurality of said samples, and temperature accuracy <0.5° C. kept amongst said samples. In various aspects, the starting fluid property is about 95° C. and 22 psi (absolute pressure) in chamber 302 at the start and reaches 55° C. and 1.5 psi (absolute pressure) at the end of cooling process. These values and those of related embodiments match the saturated condition of the working fluid. In various aspects, the saturation temperature and pressure would be different for fluids such as methanol, alcohol, fluorinated fluids, or other refrigerants used.

Referring to FIG. 7, an exemplary procedure for heating the refrigerant 314 is described as follows. As mentioned in FIG. 1, samples 300 are heated through transitions from annealing to extension and from extension to denaturing. In various aspects, samples 300 are heated to maintain constant temperature during denaturing, annealing and extension stages. Prior to heating, valve 602 is closed and samples 300 had been cooled to a predetermined temperature. Then, heater 700 is turned on and the liquid of fluid 314 held in the surrounding wick 702 will become heated. At its saturation temperature, the liquid will evaporate and heat the vapor of fluid 314 inside chamber 302. As the same time, the pressure of fluid 314 will rise to its saturation state. For water, if used as fluid 314, one state may be given by 95° C. and 22 psi (absolute) during denaturing. Another state may be given by 55° C. and 1.5 psi (absolute) during annealing. In various aspects, the saturation temperature and pressure would be different for fluids such as methanol, alcohol, fluorinated fluids, or other refrigerants if used. In various aspects, the heating rate can exceed 30° C./sec, temperature uniformity of <0.1° C. and temperature accuracy <0.5° C.

The advantages of the embodiments include, without limitation, the use of phase-changing fluid to provide heating, cooling and temperature control of PCR samples. From the description, a number of advantages of various embodiments of the thermal cycling method become evident and include, but are not limited to:

a. It permits rapid heating and cooling (>+/−30° C./s) given the substantially higher heat transfer rates that are associated with surface condensation and evaporation than other convective processes (e.g. in forced or shear flow).

b. It permits uniform heating and cooling (<0.1° C. between samples) given that heat transfers at constant temperature between the plurality of samples. This is the physical property associated with the latent heat of vaporization and condensation.

c. It permits accurate temperature control (<2% within target temperature) given that the temperature and pressure is quickly and uniformly adjusted with a combination of fast-acting valves and heaters.

d. It obviates the need for a metal substrate typically used in prior systems to retain the analyte samples. Without the solid substrate, heat is conducted directly to and from the sample vessels for heating and cooling. This thus speed up the thermal cycles dramatically over conventional substrate-based systems.

e. It differentiates from other systems by which thermal cycling is controlled by changing pressure to permit fluid phase change. This method differs from those prior systems based on heat convection using forced air or liquid flows. The method also differs from prior systems based on heat conduction using thermoelectric modules or resistive heating elements. The advantage is that pressure can be modified quicker and more uniformly than prior heating and cooling methods of using forced convection and conduction.

f. Furthermore, the present embodiments can operate in a closed cycle, where the working refrigerant fluid is passed from the hot chamber to the reactant chamber, to the cold chamber, and back to the hot chamber. This close cycle recovers the energy used in heating and cooling. In comparison, this is more efficient than other convection or conduction methods where energy is dissipated or wasted to the surrounding.

g. Another advantage of one or more aspects is related to the use of a seal to prevent vapor leakage, thereby mitigating the possibilities of cross contamination with the refrigerant fluid. The top loading of sample vessels also allows the use of already-established PCR procedures without modifications. No additives are required to modify the analyte samples to increase susceptibility to thermal, electrical or magnetic driving forces.

Accordingly, given that the disclosed thermal cycling systems, devices, and methods can use the same top-loading procedure as prior systems, new users can follow his/her original procedures without modification. Likewise, the systems, devise, and methods described herein can be configured with known, optional components such as fluorescent light detection can be adopted for real-time PCR detection methods. An optional heated lid can also prevent condensation inside the sample vessels.

In some embodiments, the disclosed systems, devices, and methods employ a thermal cycler that operates in a thermodynamic cycle, which alters both the temperature and pressure of a working refrigerant. In one embodiment, the working fluid changes phase from liquid to vapor during cooling and vapor to liquid during heating. The phase change occurs at the outward-facing surface of one or more sample vessels, which may contain reactants that are sensitive to different temperatures. In one embodiment, a wick structure is used to extend the surface of the sample vessels to trap more fluids during condensation and prevent dry-out. In one embodiment, more than one hot or one cold fluid chamber may be used for more accurate temperature control. In another embodiment, many working fluid chambers may be connected in parallel, e.g. forming a daisy-chain, to improve throughput. In another embodiment, the thermal cycler technology is used in conjunction with an optical system that can detect and quantify any changes to the reactant samples in real-time. In various embodiments, the disclosed thermal cycler method is not limited by the use in PCR analysis. The method is applicable to systems where fast temperature control is needed, including, but are not limited by, liquid viscosity measurement or thermal annealing/fatigue testers of solid-state devices.

In some embodiments, the disclosed systems, devices, and methods also comprise various embodiments that include add-ons or external elements that improve the overall PCR process. One or more of these elements include components that optically excite the sample material and detect the emitted fluorescent light. Various aspect of an optical component is to provide an excited beam of light into the sample vessels through the lid. The same optical component then collects the fluorescent light emission emitted from the sample material. The optical component then digitizes the data and displays them electronically or on paper. The advantage of an optical component is to quantify the progress of PCR during thermal cycling. This method is commonly referred to as real-time PCR or quantitative PCR.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

I claim:

1. A thermal cycling apparatus, comprising:
    a) first, second, and third insulated pressure chambers;
    b) a fluid capable of changing phases in said first and second insulated pressure chambers;
    c) a pump or compressor that maintains a pressure difference between said first and second chambers; and
    d) a first one-way or two-way valve connecting said first insulated pressure chamber to said third insulated pressure chamber and a second one-way or two-way valve connecting said second insulated pressure chamber to said third insulated pressure chamber;
    wherein said fluid in said first insulated pressure chamber is a low-pressure vapor or vapor-liquid mixture maintained at low temperature; wherein said fluid in said second insulated pressure chamber is a high-pressure vapor or vapor-liquid mixture maintained at high temperature; wherein said third insulated pressure chamber holds a plurality of sample vessels in closed wells partitioned so as to not directly contact fluid in said third insulated pressure chamber; wherein said sample vessels comprise DNA segments or strands, primers, and polymerase molecules.

2. The apparatus of claim 1 wherein said third chamber has a topside surface comprising round features which may or may not extend through a wall of said third chamber.

3. The apparatus of claim 1 wherein said third chamber is rigid to substantial pressures and insulated against heat loss at substantial temperatures.

4. The apparatus of claim 1 wherein the device is surrounded by an enclosure and user-interactive switches, buttons or electronic displays.

5. The apparatus of claim 1, wherein said vessel comprises analyte samples comprising PCR amplified nucleic acid molecules.

6. The apparatus of claim 5, further comprising a component to optically excite said analyte samples and detect emitted fluorescent light.

7. The apparatus of claim 1, further comprising a component to quantify progress of PCR during thermal cycling.

* * * * *